United States Patent
Matsumoto et al.

(10) Patent No.: US 6,645,283 B1
(45) Date of Patent: Nov. 11, 2003

(54) ANTHRAPYRIDONE COMPOUNDS, WATER-BASED MAGENTA INK COMPOSITION, AND METHOD OF INK-JET PRINTING

(75) Inventors: Hiroyuki Matsumoto, Saitama (JP); Takafumi Fujii, Saitama (JP); Yasuo Shirasaki, Saitama (JP); Hirokazu Kitayama, Saitama (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/786,564

(22) PCT Filed: Oct. 21, 1999

(86) PCT No.: PCT/JP99/05812

§ 371 (c)(1),
(2), (4) Date: Mar. 7, 2001

(87) PCT Pub. No.: WO00/23440

PCT Pub. Date: Apr. 27, 2000

(30) Foreign Application Priority Data

Oct. 22, 1998 (JP) .......................................... 10-301254

(51) Int. Cl.[7] ...................... C09D 11/02; C07D 221/18; C07D 401/12; C09B 5/14
(52) U.S. Cl. ..................................... 106/31.47; 546/76
(58) Field of Search .......................... 106/31.47; 546/76

(56) References Cited

U.S. PATENT DOCUMENTS

| | | | | |
|---|---|---|---|---|
| 2,644,821 A | | 7/1953 | Peter et al. ................. | 260/278 |
| 2,962,497 A | | 11/1960 | Guenthard .................. | 260/249 |
| 4,198,205 A | | 4/1980 | Elser et al. .................. | 8/39 R |
| 4,975,094 A | | 12/1990 | Miki et al. .................... | 8/537 |
| 6,152,969 A | * | 11/2000 | Matsumoto et al. .......... | 546/76 |

FOREIGN PATENT DOCUMENTS

| | | | |
|---|---|---|---|
| CH | 365471 | 12/1962 | |
| EP | 1067155 A1 * | 1/2001 | ............. C09B/5/14 |
| EP | 1123932 A1 * | 8/2001 | ......... C07D/401/12 |
| JP | 57-195775 | 12/1982 | |
| JP | 57-197191 | 12/1982 | |
| JP | 59-074173 | 4/1984 | |
| JP | 2-16171 | 1/1990 | |
| JP | 2-132159 | 5/1990 | |
| JP | 3-100502 | 4/1991 | |
| JP | 8-29771 | 2/1996 | |
| WO | 99/48981 | 9/1999 | |
| WO | WO00/23440 | * 4/2000 | |

* cited by examiner

Primary Examiner—Helene Klemanski
(74) Attorney, Agent, or Firm—Nields & Lemack

(57) ABSTRACT

The present invention relates to a novel anthrapyridone compound represented by Formula (1) as described below or the salt thereof which has hue and vividness suitable for ink-jet printing and give a print excellent in fastness to light and water, a water-based magenta ink composition containing any of the compounds or salt thereof, an ink-jet printing method using the ink composition and a new intermediate.

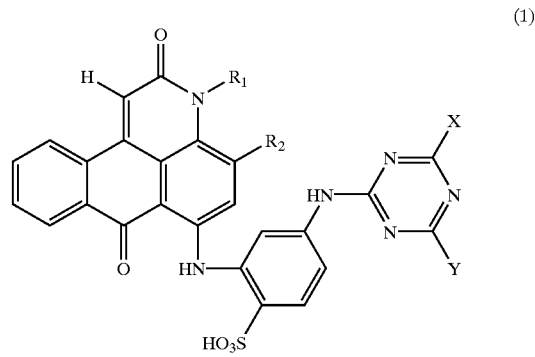

(1)

wherein, $R_1$ is hydrogen atom, an alkyl group etc; $R_2$ is hydrogen atom, methyl etc; X and Y represent independently chlorine atom, hydroxy, etc.

20 Claims, No Drawings

ANTHRAPYRIDONE COMPOUNDS, WATER-BASED MAGENTA INK COMPOSITION, AND METHOD OF INK-JET PRINTING

TECHNICAL FIELD

The present invention relates to a novel anthrapyridone compound, a water-based magenta ink composition, and a method of ink-jet recording.

BACKGROUND ART

Diverse ink jetting processes have been developed for the recording method by means of ink-jet printer, and any process comprises generating ink droplets to deposit them onto various recording materials (such as paper, film, cloth) for recording. The recording method by means of ink-jet printer has rapidly been spread in recent years and will be propagated in future because the method brings about no noise due to the system in which a recording head does not contact with the recording material and because the method advantageously allows the printer to become downsized, to work in a high-speed and to give color printing, easily. For recording an image information or a character information pictured on a computer color display in color by means of an ink-jet printer, the information is generally printed according to subtractive color mixing of inks of four colors, namely yellow(Y), magenta(M), cyan(C) and black(K). In order to print reproductively an image pictured by additive color mixing of R(red), G(green), B(blue) on a CRT display as faithfully as possible according to subtractive color mixing, the dyestuffs used, especially ones for a YMC ink, are desired to have color hues close to the respective standards of YMC ("Japan Color Standard Paper" published by Japan Printing Machinery Manufacturers Association) and vividness. Additionally, it is required that the resulting ink composition is stable for long-term storage and that the resulting printed image is of a high optical density and has excellent fastness including water fastness and light fastness.

Ink-jet printers are increasingly used in a wide range from a small one for OA use to a big one for industrial use. So, excellence in fastness such as water fastness and light fastness of the printed image is more strictly demanded. The water fastness is substantially improved by coating inorganic micro particles such as porous silica, cationic polymer, alumina sol, special ceramic which can absorb dyestuff from ink, on a paper sheet together with PVA resin. Various coated sheets for ink-jet printing are already available on the market. But light fastness is not yet improved by any established technique. Of tetrachromatic colors of YMCK, magenta especially has many dyestuffs which are naturally weak in light fastness, and the improvement is an important problem to be solved.

The typical types of chemical structure of magenta dyestuffs used in a water-soluble ink for ink-jet recording are a xanthene type disclosed by JP Laid-Open No.89811/1979, JP Laid-Open No.60053/1996 and JP Laid-Open No.143798/1996 etc., or an azo type using the H acid disclosed by JP Laid-Open No.62562/1986, JP Laid-Open No.156168/1987, JP Laid-Open No.203970/1991, JP Laid-Open No.157698/1995 and JP Publication No.78190/1995 etc. The xanthene type is indeed excellent in hue and vividness, but is inferior in light fastness. The azo type using the H acid is good in hue and water fastness, but is inferior in light fastness and vividness. As disclosed by JP Laid-Open No.203970/1991, for example, some magenta dyestuffs in this type being excellent in vividness and light fastness have been developed, but are still inferior in light fastness to dyestuffs having other hue such as, typically, yellow dyestuffs and cyan dyestuffs which are copper phthalocyanine type.

Furthermore, for a chemical structure of magenta dyes excellent in vividness and light fastness, an anthrapyridone type is known as disclosed by JP Laid-Open No.74173/1984 and JP Laid-Open No.16171/1990, but can not yet show any satisfactory properties in hue, vividness, light fastness, water fastness and stability in solution.

An object of the present invention is to provide a magenta dye which has hue and vividness suitable for ink-jet recording and supplies the recorded material with a high fastness in light fastness and water fastness.

DISCLOSURE OF THE INVENTION

The present inventors made a diligent study to solve the above problem and, as a result, have completed the present invention. Namely, the present invention is as follows:

A novel anthrapyridone compound represented by Formula (1) as described below or the salt thereof

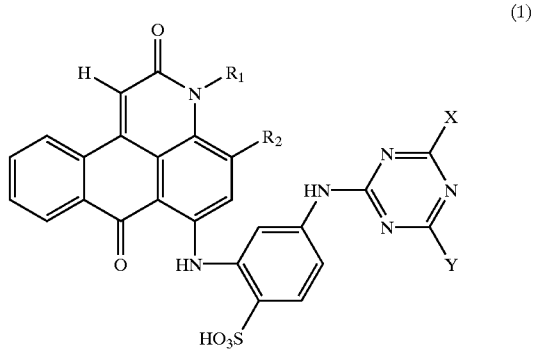

(1)

(wherein, $R_1$ is hydrogen, an alkyl group, a hydroxy lower alkyl group, cyclohexyl, a mono- or di-alkylaminoalkyl group, or a cyano lower alkyl group; $R_2$ is hydrogen, methyl, ethyl, phenoxy (which may be substituted), sulfo or carboxy; X and Y represent independently chloro, hydroxy, an alkoxy group, phenoxy (which may be substituted with the substituents selected from the group consisting of sulfo, carboxy, acetylamino, amino, and hydroxy), a mono- or di-alkylamino group having sulfo or carboxy, anilino (which may be substituted with one or two substituents selected from the group consisting of sulfo and carboxy), naphthylamino (the naphthyl may be substituted with sulfo), or a mono- or di-alkylaminoalkylamino group, except that X and Y are respectively any groups selected from chloro, hydroxy and anilino (which may be substituted with one or two substituents selected from the group consisting of sulfo and carboxy) if $R_2$ is hydrogen.)

[2] A novel anthrapyridone compound or the salt thereof according to the above [1], wherein said compound is represented by Formula (2) as described below:

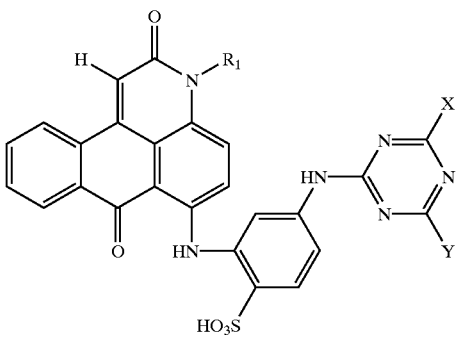

(wherein, $R_1$ is hydrogen or an alkyl group; X and Y represent independently chloro, hydroxy, an alkoxy group, phenoxy (which may be substituted with the substituents selected from the group consisting of sulfo, carboxy, acetylamino, amino, and hydroxy), an alkylamino group having sulfo or carboxy, anilino (which may be substituted with one or two substituents selected from the group consisting of sulfo and carboxy), naphthylamino (the naphthyl may be substituted with sulfo), or a dialkylaminoalkylamino group, except that X and Y are respectively any groups selected from choloro, hydroxy, and anilino (which may be substituted with one or two substituents selected from the group consisting of sulfo and carboxy).)

[3] A novel anthrapyridone compound or the salt thereof according to the above [1] or [2], wherein X is anilino (which may be substituted with one or two substituents selected from the group consisting of sulfo and carboxy) or naphthylamino (the naphthyl may be substituted with sulfo); and Y is chloro, hydroxy, an alkoxy group, phenoxy (which may be substituted with the substituents selected from the group consisting of sulfo, carboxy, acetylamino, amino, and hydroxy), anilino (which may be substituted with one or two substituents selected from the group consisting of sulfo and carboxy), an alkylamino group having sulfo or carboxy, or a dialkylaminoalkylamino group.

[4] A novel anthrapyridone compound or the salt thereof according to the above [1] or [2], wherein $R_1$ is hydrogen or methyl; X is anilino substituted with one or two substituents selected from sulfo and carboxy; and Y is hydroxy, methoxy, phenoxy (which may be substituted with the substituents selected from the group consisting of sulfo, carboxy, acetylamino, amino, and hydroxy), anilino having sulfo, an alkylamino group having sulfo or carboxy, or a dialkylaminoalkylamino group.

[5] A novel anthrapyridone compound or the salt thereof according to the above [1] or [2], wherein X is naphthylamino substituted with sulfo; and Y is chloro, hydroxy, methoxy, phenoxy (which maybe substituted with the substituents selected from the group consisting of sulfo, carboxy, acetylamino, amino, and hydroxy), or an alkylamino group having sulfo or carboxy.

[6] A novel anthrapyridone compound or the salt thereof according to the above [1] or [2], wherein $R_1$ is hydrogen or methyl; X is naphthylamino substituted with three sulfo groups; and Y is chloro, hydroxy, or phenoxy.

[7] A novel anthrapyridone compound or the salt thereof according to the above [6], wherein said naphthylamino substituted with three sulfo groups is the 2-naphthylamino or 1-naphthylamino that has said three sulfo groups at the 3-, 6-, and 8-positions or at the 4-, 6-, and 8-positions.

[8] A novel anthrapyridone compound represented by Formula (1) or (2) or the salt thereof, wherein $R_1$ is hydrogen or methyl; $R_2$ is hydrogen, methyl, ethyl, phenoxy (which may be substituted), sulfo or carboxy; X is anilino having two carboxy groups; and Y is hydroxy, anilino having two sulfo groups, an alkylamino group having sulfo or carboxy, or a dialkylaminoalkylamino group.

[9] A novel anthrapyridone compound or the salt thereof according to the above [8], wherein said anilino having two carboxy groups is 3,5-dicarboxyanilino, said alkylamino group having sulfo or carboxy is 2-sulfoethylamino, carboxymethylamino, 2-carboxyethylamino or 1-carboxyethyl-amino, diethylaminoethylamino or diethylaminopropylamino.

[10] A water-based magenta ink composition that contains the anthrapyridone compound or the salt thereof according to any one of the above [1] to [9] as a dyestuff component.

[11] A water-based magenta ink composition according to the above [10], wherein said composition contains an organic solvent.

[12] A water-based magenta ink composition according to the above [10] or [11], wherein the content of inorganic salt included in the dyestuff component is 1% or less by mass.

[13] A water-based magenta ink composition according to any one of the above [10] to [12], wherein said composition is prepared for ink-jet recording.

[14] A method for ink-jet recording which comprises using the water-based magenta ink composition according to any one of the above [10] to [13] as an ink, in the recording way that ink droplets are ejected responding to record signals to record onto a recording material.

[15] A method for ink-jet recording according to the above [14], wherein said recording material is an information transmission sheet.

[16] A container holding the water-based magenta ink composition according to any one of the above [10] to [13].

[17] An ink-jet printer equipped with the container according to the above [16].

[18] A colored article including the anthrapyridone compound or the salt thereof according to any one of the above [1] to [9].

[19] An anthrapyridone compound represented by Formula (5) as shown below:

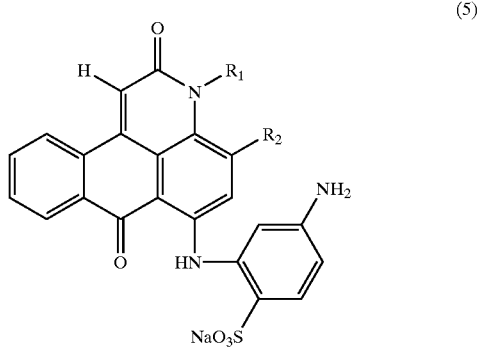

(wherein, $R_1$ and $R_2$ show their same respective meanings as in Formula(1), except that if $R_1$ is hydrogen or methyl, $R_2$ is hydrogen.)

[20] An anthrapyridone compound represented by Formula (6) as shown below:

(6)

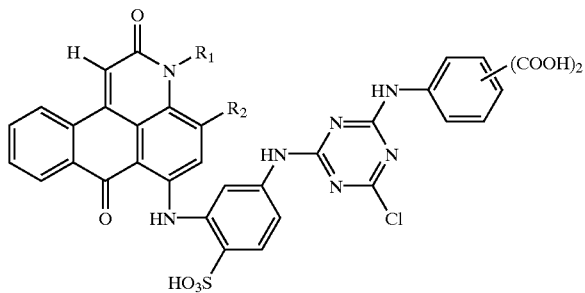

(wherein, $R_1$ is hydrogen, an alkyl group, hydroxyethyl, cyclohexyl, a dialkylaminoalkyl group or cyanoethyl; $R_2$ is hydrogen, methyl, ethyl, phenoxy (which may be substituted), sulfo or carboxy.)

BEST MODE FOR CARRYING OUT THE INVENTION

The novel anthrapyridone compound of the present invention can be presented by Formula (1) as shown above.

An alkyl in the "alkyl" or "alkoxy" in the present invention is preferably, but not limited to, a C1 to C10 alkyl group, and the "lower alkyl" or "lower alkoxy" is preferably a C1 to C4 alkyl group.

In Formula (1) as shown above, the alkyl group as $R_1$ includes a C1 to C4 alkyl group such as methyl, ethyl, n-propyl and n-butyl. The hydroxy lower alkyl group as $R_1$ includes a C1 to C4 hydroxyalkyl group such as hydroxymethyl, hydroxyethyl, hydroxy n-propyl and hydroxy n-butyl, and is preferably hydroxyethyl. The cyano lower alkyl group as $R_1$ includes a C1 to C4 cyanoalkyl group such as cyanomethyl, cyanoethyl, cyano n-propyl and cyano n-butyl, and is preferably cyanoethyl.

The phenoxy (which may be substituted) as $R_2$ includes unsubstituted phenoxy, and phenoxy having a substituent such as an alkyl group, a halogen atom, hydroxy, a lower alkoxy group, sulfo, carboxy, amino, acetylamino, or cyano. The preferable substituent is an alkyl group, particularly a branched C3 to C8 alkyl group such as isopropyl, t-butyl, t-amyl, and 1,1,3,3-tetramethylbutyl.

The alkoxy group as X or Y includes a C1 to C4 alkoxy group such as methoxy, ethoxy, n-propoxy, isopropoxy, and butoxy.

The phenoxy as X or Y, which may be substituted with the substituents selected from sulfo, carboxy, acetylamino, amino, and hydroxy, includes 4-sulfophenoxy, 4-carboxyphenoxy, 4-acetylaminophenoxy, 4-aminophenoxy, and 4-hydroxyphenoxy.

The alkyl group suggested by the alkylamino group having sulfo or carboxy in X or Y includes a C1 to C4 alkyl group such as methyl, ethyl, n-propyl and n-butyl, and is preferably methyl or ethyl. The alkylamino group having sulfo or carboxy is preferably a mono- or di-alkylamino group having one or two sulfo or carboxy such as a (mono- or di-sulfo)lower alkylamino group, a (mono- or di-carboxy) lower alkylamino group, and a di(carboxy lower alkyl) amino group. The examples are sulfomethylamino, 1- or 2-sulfoethylamino, 1-, 2- or 3-sulfopropylamino, 2,3-disulfopropylamino, carboxymethylamino, 1- or 2-carboxyethylamino, 1-, 2- or 3-carboxypropylamino, 1,2-dicarboxyethylamino, 1,2-dicarboxypropylamino, 1,3-dicarboxypropylamino, 2,3-dicarboxypropylamino, di(carboxymethyl)amino, di(carboxyethyl)amino, and di(carboxypropyl)amino. The preferable examples are 2-sulfoethylamino, carboxymethylamino, 2-carboxyethylamino, 1-carboxyethylamino, 1,2-dicarboxyethylamino, di(carboxymethyl)amino and di(carboxyethyl)amino.

Among the preferable mono- or di-alkylaminoalkyl groups in $R_1$, X and Y is a mono- or di-lower alkylamino lower alkyl group such as methylaminomethyl, methylaminoethyl, methylaminopropyl, ethylaminomethyl, ethylaminoethyl, ethylaminopropyl, dimethylaminomethyl, dimethylaminoethyl, dimethylaminopropyl, diethylaminomethyl, diethylaminoethyl, and diethylaminopropyl, The anilino as X or Y, which may be substituted with one or two substituents selected from the group consisting of sulfo and carboxy, includes 2,5- or 3,5-dicarboxyanilino, 3-carboxyanilino, 2-carboxyanilino, 4-carboxyanilino, 2,5- or 3,5-disulfoanilino, 3-sulfoanilino, 2-sulfoanilino, 4-sulfoanilino, 2-carboxy-4-sulfoanilino, and 2-carboxy-5-sulfoanilino. The preferable anilino is an anilino having two substituents, particularly having two carboxy groups.

The preferable naphthylamino as X or Y, which may be substituted with sulfo, is naphthylamino substituted with two or three sulfo groups such as 3,6,8-trisulfo-1-naphthylamino, 4,6,8-trisulfo-2-naphthylamino, 3,6,8-trisulfo-2-naphthylamino, and 4,8-disulfo-2-naphthylamino.

The X is preferably anilino having at least one, more preferably two or more carboxy or sulfo groups, and particularly two carboxy groups. The Y is preferably a C1–C4 alkylamino having carboxy or sulfo as the substituent. The combinations of these X and Y are more preferable.

The preferable combination of $R_1$, X and Y is, for example, a combination wherein $R_1$ is hydrogen or methyl; X is anilino (which may be substituted with one or two substituents selected from the group consisting of sulfo and carboxy), preferably anilino having at least one, more preferably two or more carboxy or sulfo, particularly anilino having two carboxy groups, or naphthylamino (the naphthyl may be substituted with sulfo), preferably naphthylamino substituted with two or three sulfo groups; and Y is chloro, hydroxy, an alkoxy group, phenoxy (which may be substituted with the substituents selected from the group consisting of sulfo, carboxy, acetylamino, amino, and hydroxy), anilino (which may be substituted with one or two substituents selected from the group consisting of sulfo and carboxy), or alkylamino group having sulfo or carboxy, and is preferably chloro or a C1–C4 alkylamino group having carboxy or sulfo as the substituent.

The more preferable combination of $R_1$, X and Y is, for example, a combination wherein $R_1$ is hydrogen or methyl; X is anilino substituted with one or two substituents selected from the group consisting of sulfo and carboxy; and Y is hydroxy, methoxy, phenoxy (which may be substituted with the substituents selected from the group consisting of sulfo, carboxy, acetylamino, amino, and hydroxy), anilino having sulfo, or alkylamino group having sulfo or carboxy.

The most preferable combination of $R_1$, X and Y is, for example, a combination wherein $R_1$ is hydrogen or methyl; X is anilino having two carboxy groups; and Y is anilino having hydroxy and/or two sulfo groups, or alkylamino group having sulfo or carboxy. The anilino having two carboxy groups is preferably 3,5-dicarboxyanilino. The alkylamino group having sulfo or carboxy is preferably 2-sulfoethylamino, carboxymethylamino, or 2-carboxyethylamino.

The alternative preferable combination of $R_1$, X and Y is, for example, a combination wherein $R_1$ is hydrogen or methyl; X is naphthylamino substituted with sulfo; and Y is chloro, hydroxy, methoxy, phenoxy (which may be substituted with the substituents selected from the group consisting of sulfo, carboxy, acetylamino, amino, and hydroxy), or alkylamino group having sulfo or carboxy.

The alternative more preferable combination of $R_1$, X and Y is, for example, a combination wherein $R_1$ is hydrogen or methyl; X is naphthylamino substituted with three sulfo groups; and Y is chloro, hydroxy, or phenoxy. The naphthylamino substituted with three sulfo groups is preferably 2-naphthylamino or 1-naphthylamino having the sulfo groups at their 3,6,8-positions or 4,6,8-positions.

The examples of the novel anthrapyridone compound represented by Formula (1) of the present invention are shown in Table 1. In Table 1, (S) means sulfo, (K) means carboxy, and a numeral described just prior to (S) or (K) means the number of their substituents.

TABLE 1

| No. | $R_1$ | $R_2$ | X | Y |
|---|---|---|---|---|
| 1 | $CH_3$ | H | 3,5-2(K)-anilino | Cl |
| 2 | $CH_3$ | H | 3,5-2(K)-anilino | 2-sulfoethylamino |
| 3 | $CH_3$ | H | 2,5-2(K)-anilino | Cl |
| 4 | $CH_3$ | H | 2,5-2(K)-anilino | 2-sulfoethylamino |
| 5 | $CH_3$ | H | 3,5-2(K)-anilino | carboxymethylamino |
| 6 | $CH_3$ | H | 3,5-2(K)-anilino | 2-carboxyethylamino |
| 7 | $CH_3$ | H | 3,5-2(K)-anilino | 1-carboxyethylamino |
| 8 | $CH_3$ | H | 3,5-2(K)-anilino | 1,2-dicarboxyethylamino |
| 9 | $CH_3$ | H | 3,5-2(K)-anilino | 1,3-dicarboxypropylamino |
| 10 | $CH_3$ | H | 2,5-2(K)-anilino | carboxymethylamino |
| 11 | $CH_3$ | H | 2,5-2(K)-anilino | 2-carboxyethylamino |
| 12 | $CH_3$ | H | 2,5-2(K)-anilino | 1-carboxyethylamino |
| 13 | $CH_3$ | H | 2,5-2(K)-anilino | 1,2-dicarboxyethylamino |
| 14 | $CH_3$ | H | 2,5-2(K)-anilino | 1,3-dicarboxypropylamino |
| 15 | $CH_3$ | H | 3,6,8-3(S)-2-naphthylamino | Cl |
| 16 | $CH_3$ | H | 3,6,8-3(S)-2-naphthylamino | OH |
| 17 | $CH_3$ | H | 3,6,8-3(S)-2-naphthylamino | phenoxy |
| 18 | $CH_3$ | H | 3,6,8-3(S)-2-naphthylamino | methoxy |
| 19 | $CH_3$ | H | 4,6,8-3(S)-2-naphthylamino | Cl |
| 20 | $CH_3$ | H | 4,6,8-3(S)-2-naphthylamino | OH |
| 21 | $CH_3$ | H | 4,6,8-3(S)-2-naphthylamino | phenoxy |
| 22 | $CH_3$ | H | 4,6,8-3(S)-2-naphthylamino | methoxy |
| 23 | $CH_3$ | H | 3,6,8-3(S)-1-naphthylamino | OH |
| 24 | $CH_3$ | H | 3,6,8-3(S)-1-naphthylamino | phenoxy |
| 25 | $CH_3$ | H | 4,8-2(S)-2-naphthylamino | OH |
| 26 | $CH_3$ | H | 2,5-2(S)-anilino | methoxy |
| 27 | $CH_3$ | H | 2,5-2(S)-anilino | phenoxy |
| 28 | $CH_3$ | H | 2,5-2(S)-anilino | 4-(S)-phenoxy |
| 29 | $CH_3$ | H | 2,5-2(S)-anilino | 4-acetylaminophenoxy |
| 30 | $CH_3$ | H | 2,5-2(S)-anilino | 4-aminophenoxy |
| 31 | H | H | 3,5-2(K)-anilino | 2-sulfoethylamino |
| 32 | H | H | 2,5-2(K)-anilino | 2-sulfoethylamino |
| 33 | H | H | 3,5-2(K)-anilino | carboxymethylamino |
| 34 | H | H | 3,5-2(K)-anilino | 2-carboxyethylamino |
| 35 | H | H | 3,5-2(K)-anilino | 1-carboxyethylamino |
| 36 | H | H | 3,5-2(K)-anilino | 1,2-dicarboxyethylamino |
| 37 | H | H | 3,5-2(K)-anilino | 1,3-dicarboxypropylamino |
| 38 | H | H | 2,5-2(K)-anilino | carboxymethylamino |
| 39 | H | H | 2,5-2(K)-anilino | 2-carboxyethylamino |
| 40 | H | H | 2,5-2(K)-anilino | 1-carboxyethylamino |
| 41 | H | H | 2,5-2(K)-anilino | 1,2-dicarboxyethylamino |
| 42 | H | H | 2,5-2(K)-anilino | 1,3-dicarboxypropylamino |
| 43 | H | H | 3,6,8-3(S)-2-naphthylamino | Cl |
| 44 | H | H | 3,6,8-3(S)-2-naphthylamino | OH |
| 45 | H | H | 3,6,8-3(S)-2-naphthylamino | phenoxy |
| 46 | H | H | 3,6,8-3(S)-2-naphthylamino | methoxy |
| 47 | H | H | 4,6,8-3(S)-2-naphthylamino | Cl |
| 48 | H | H | 4,6,8-3(S)-2-naphthylamino | OH |
| 49 | H | H | 4,6,8-3(S)-2-naphthylamino | phenoxy |
| 50 | H | H | 4,6,8-3(S)-2-naphthylamino | methoxy |
| 51 | H | H | 3,6,8-3(S)-1-naphthylamino | Cl |
| 52 | H | H | 3,6,8-3(S)-1-naphthylamino | OH |
| 53 | H | H | 4,8-2(S)-2-naphthylamino | OH |
| 54 | $C_2H_5$ | H | 3,5-2(K)-anilino | 2-sulfoethylamino |
| 55 | $C_2H_5$ | H | 3,5-2(K)-anilino | carboxymethylamino |
| 56 | $C_2H_5$ | H | 3,5-2(K)-anilino | 2-carboxyethylamino |
| 57 | $C_2H_5$ | H | 3,6,8-3(S)-2-naphthylamino | Cl |
| 58 | $C_2H_5$ | H | 3,6,8-3(S)-2-naphthylamino | OH |
| 59 | $C_2H_5$ | H | 4,6,8-3(S)-2-naphthylamino | Cl |
| 60 | $C_2H_5$ | H | 4,6,8-3(S)-2-naphthylamino | OH |
| 61 | $C_4H_9$ | H | 3,5-2(K)-anilino | 2-sulfoethylamino |
| 62 | $C_4H_9$ | H | 3,5-2(K)-anilino | carboxymethylamino |
| 63 | $C_4H_9$ | H | 3,5-2(K)-anilino | 2-carboxyethylamino |

TABLE 1-continued

| No. | $R_1$ | $R_2$ | X | Y |
|---|---|---|---|---|
| 64 | $C_4H_9$ | H | 3,6,8-3(S)-2-naphthylamino | OH |
| 65 | $C_4H_9$ | H | 4,6,8-3(S)-2-naphthylamino | OH |
| 66 | $CH_3$ | $CH_3$ | 2,5-2(S)-anilino | OH |
| 67 | H | $CH_3$ | 2,5-2(S)-anilino | OH |
| 68 | $CH_3$ | $CH_3$ | 3,5-2(K)-anilino | 2-sulfoethylamino |
| 69 | H | $CH_3$ | 3,5-2(K)-anilino | 2-sulfoethylamino |
| 70 | $CH_3$ | $CH_3$ | 3,6,8-3(S)-2-naphthylamino | Cl |
| 71 | $CH_3$ | $CH_3$ | 3,6,8-3(S)-2-naphthylamino | OH |
| 72 | $CH_3$ | $C_2H_5$ | 2,5-2(S)-anilino | OH |
| 73 | H | $C_2H_5$ | 2,5-2(S)-anilino | OH |
| 74 | $CH_3$ | OPh | 2,5-2(S)-anilino | OH |
| 75 | H | OPh | 2,5-2(S)-anilino | OH |
| 76 | H | $OPhC(CH_3)_3$ | 2,5-2(S)-anilino | OH |
| 77 | H | $OPhC(CH_3)_2C_2H_5$ | 2,5-2(S)-anilino | OH |
| 78 | H | $OPhC(CH_3)_2CH_2C(CH_3)_3$ | 2,5-2(S)-anilino | OH |
| 79 | H | $SO_3H$ | 2,5-2(S)-anilino | OH |
| 80 | H | COOH | 2,5-2(S)-anilino | OH |
| 81 | $C_2H_5$ | H | 2,5-2(S)-anilino | OH |
| 82 | $CH(CH_3)_2$ | H | 2,5-2(S)-anilino | OH |
| 83 | cyclohexyl | H | 2,5-2(S)-anilino | OH |
| 84 | $C_2H_4OH$ | H | 2,5-2(S)-anilino | OH |
| 85 | $C_2H_4CN$ | H | 2,5-2(S)-anilino | OH |
| 86 | $C_3H_6N(C_2H_5)_2$ | H | 2,5-2(S)-anilino | OH |
| 87 | $C_2H_4N(C_2H_5)_2$ | H | 2,5-2(S)-anilino | OH |
| 88 | $CH_3$ | H | 3,5-2(K)-anilino | $NHC_3H_6N(C_2H_5)_2$ |
| 89 | $CH_3$ | H | 3,5-2(K)-anilino | $NHC_2H_4N(C_2H_5)_2$ |
| 90 | $CH_3$ | H | 3,5-2(K)-anilino | $N(CH_2COOH)_2$ |
| 91 | $CH_3$ | H | 3,5-2(K)-anilino | OH |
| 92 | $CH_3$ | H | 3,5-2(K)-anilino | 2,5-2(S)-anilino | note)
In the table, Ph represents phenyl.

In order to obtain the compound represented by Formula (1), 1 mol of the corresponding anilines or naphthylamines, for example, is reacted with 0.9–1.1 mol of 2,4,6-trichloro-s-triazine (cyanuric chloride) in water at pH 3–6 at 0–10° C. for 2–4 hrs to give the first condensate, which is then reacted with 0.8–0.9 mol of an aminoanthrapyridone of Formula (5) as described above at pH 4–9 at 50–70° C. for 2–5 hrs to give the second condensate wherein Y is chloro. The second condensate is either hydrolyzed at pH 9–12 at 70–90° C. for 1–5 hrs, or reacted with corresponding amines, phenols or alcohols such as methanol at pH 8–9 at 90–100° C. for 3–8 hrs to obtain the third condensate wherein Y is an other group than chloro. Order of the condensation may be determined depending on the reactivities of the related compounds, but is not limited to the above order.

The compound thus obtained exists as a free acid or the salt thereof. The free acid or the salt thereof can be used in the present invention. The salt can be used as the alkali metal salt, the alkali earth metal salt, the alkylamine salt, the alkanolamine salt or the ammonium salt. The preferable salt includes an alkali metal salt such as the sodium salt, the potassium salt and the lithium salt; an alkanolamine salt such as the monoethanolamine salt, the diethanolamine salt, the triethanolamine salt, the monoisopropanolamine salt, the diisopropanolamine salt and the triisopropanolamine salt; and the ammonium salt. For preparing, sodium chloride is added, for example, to the reaction solution of the above third condensate followed by salting out and filtrating to obtain the sodium salt as a wet cake, which is again dissolved in water followed by adding hydrochloric acid to adjust the pH to 1–2. The deposited crystal is filtered to obtain the free acid (which may partly include the sodium salt). While the free acid as a wet cake is stirred in water, potassium hydroxide, lithium hydroxide or aqueous ammonia for example is added to alkalize to obtain the potassium salt, the lithium salt or the ammonium salt respectively.

The anthrapyridone compound of Formula (5) can be obtained for example by the following process:

1 mol of the bromoanthrapyridone of Formula (3) as illustrated below is condensed with 1.1–5 mol of 5-acetylamino-2-sulfoaniline in a non-proton polar organic solvent such as DMF (dimethylformamide) under the presence of a deacidification agent such as sodium carbonate and a copper catalyst such as copper acetate at 120–140° for 2–5 hrs by way of the Ullmann reaction to obtain a compound of Formula (4) as illustrated below. The compound thus obtained is hydrolyzed under the presence of a strong acid such as sulfuric acid at 90–130° C. to remove the acetyl group to obtain the anthrapyridone of Formula (5).

(3)

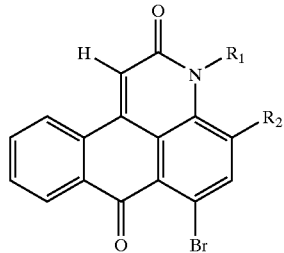

-continued (4)

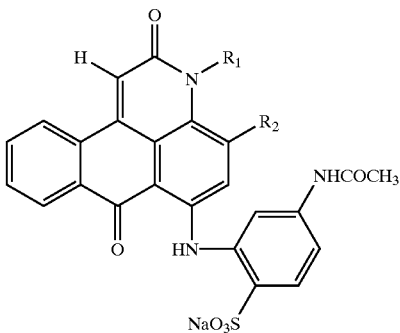

(wherein, $R_1$ and $R_2$ respectively are same as in Formula (1))

The water-based magenta ink composition of the present invention can be obtained by dissolving the compound represented by Formula (1) or (2) or the salt thereof in water or a hydrous solvent [water containing a water-soluble organic solvent (including a solubilizer) which will be described later]. The preferable ink pH is about 6 to 11. For use in an ink-jet recording printer, it is preferable to use a water-based ink composition whose dyestuff component contains an amount as little as possible of an inorganic material such as the chloride and the sulfate of a metal positive ion. For example, the total content of sodium chloride and sodium sulfate in the dyestuff component is 1% by mass or less relative to the total amount of the dyestuff component.

In order to produce the dyestuff component of the present invention having a low content of inorganic salt, it is sufficient to repeat a desalting treatment, for example, by a conventional method such as reverse osmotic membrane or by stirring a dry product or a wet cake of the anthrapyridone of the present invention in a mixed solvent of methanol and water, then filtering and drying.

The water-based ink composition of the present invention is prepared by using water as a medium, containing the anthrapyridone compound or the salt thereof preferably by 0.1 to 20% by mass, more preferably by 1 to 10% by mass, more preferably 2 to 8% by mass. The water-based ink composition of the present invention also may contain a water-soluble organic solvent by 0–30% by mass and ink regulators by 0 to 5% by mass.

The ink composition of the present invention is prepared by adding the compound or its salt of the present invention, the above water-soluble organic solvent and the ink regulators if necessary into purified water such as distilled water and mixing them together. Alternatively, the compound or its salt of the present invention may be added in a mixture of water, the above water-soluble organic solvent and the ink regulators to dissolve. The resulting ink composition may be filtered, if necessary, to remove the contaminants from the composition.

The usable water-soluble organic solvent includes a C1–C4 alkanol such as methanol, ethanol, propanol, isopropanol, butanol, isobutanol, secondary butanol and tertiary butanol; a carboxylic amide such as N,N-dimethylformamide and N,N-dimethylacetoamide; a lactam such as ε-caprolactam and N-methylpyrrolidin-2-one; urea; a cyclic urea such as 1,3-dimetylimidazolidin-2-one or 1,3-dimethylhexahydropyrimid-2-one; a ketone or a keto-alcohol such as acetone, methyl ethyl ketone, and 2-methyl-2-hydroxypentan-4-one; an ether such as tetrahydrofuran and dioxane; mono-, oligo- or poly-alkylene glycol or thioglycol having C2–C6 alkylene units, such as ethylene glycol, 1,2- or 1,3-propylene glycol, 1,2- or 1,4-butylene glycol, 1,6-hexylene glycol, diethylene glycol, triethylene glycol, dipropylene glycol, thiodiglycol, polyethylene glycol and polypropylene glycol; polyols(triols) such as glycerin and hexane-1,2,6-triol; C1–C4 alkyl ethers of polyhydric alcohols, such as ethylene glycol monomethyl ether, ethylene glycol monoethyl ether, diethylene glycol monomethyl ether, diethylene glycol monoethyl ether, triethylene glycol monomethyl ether, and triethylene glycol monoethyl ether; γ-butyrolactone; and dimethylsulfoxide. These solvents may be used in a combination of the two or more.

The favorable examples of water-miscible organic solvents are N-methylpyrrolidin-2-one and mono-, di- or trialkylene glycol having C2–C6 alkylene units, preferably mono-, di- or triethylene glycol, dipropylene glycol and dimethylsulfoxide. N-methylpyrrolidin-2-one, diethylene glycol, and dimethyl-sulfoxide are especially preferably used.

The ink regulators, which are used to provide the aqueous solution containing the compound of the present invention (a dyestuff component) with a desired ink properties, include a preservative, a pH adjusting agent, a chelating agent, a rust preventive, a water-soluble ultraviolet absorbing agent, a water-soluble polymeric compound, and a surfactant. The preservative includes sodium dehydroacetate, sodium sorbate, sodium 2-pyridinethiol-1-oxide, sodium benzoate and sodium pentachlorophenol. The pH adjusting agent includes any substance that can control the ink pH within a range of 6 to 11 with no adverse effect on the ink preparation. The examples are alkanolamines such as diethanolamine and triethanolamine; alkali metal hydroxides such as lithium hydroxide, sodium hydroxide, and potassium hydroxide; ammonium hydroxide; or alkali metal carbonates such as lithium carbonate, sodium carbonate and potassium carbonate. The chelating reagent includes sodium ethylenediaminetetraacetate, sodium nitrilotriacetate, sodium hydroxylethylenediaminetriacetate, sodium diethylenetriaminepentaacetate, and sodium uramil diacetate. The rust preventive includes acidic hyposulfite salts, sodium thiosulfate, ammonium thioglycolate, diisopropylammonium nitrite, tetranitrate pentaerythritol, and dicyclohexylammonium nitrite.

A recording material used in ink-jet recording includes an information transmission sheet such as paper and film, fiber and leather. It is preferable that the information transmission sheet is surface-treated and, practically, is coated with an ink-acceptable layer on the basement material. The ink-acceptable layer can be prepared, for example, by impregnating or coating a cationic polymer on the above basement material; or by coating an inorganic fine-particles being enable of absorbing the dyestuff from an ink such as porous silica, alumina sol and special ceramic together with a hydrophilic polymer such as polyvinyl alcohol and polyvinyl pyrrolidone on the surface of the above basement material. The sheet having the ink-acceptable layer is generally called an ink-jet special paper (film) or a glossy paper (film), and is available on the market, for example, as Pictorico (trade name) (by Asahi Glass KK), Color BJ Paper, Color BJ Photofilm sheet (trade name) (by Canon KK), Color Image Jet special paper (trade name) (by Sharp KK), Superfine special glossy film (trade name) (by Seiko Epson KK) and Pictafine (trade name) (by Hitachi Maxell KK). A plain paper can be of course used also.

The preferable fiber is a polyamide fiber such as nylon, silk and wool in nonwoven fabric or cloth. The ink composition of the present invention is applied, preferably by ink-jet, to the fiber followed by fixing by wet heat (for example, about 80–120° C.) or dry heat (for example, about 150–180° C.), so that the dyestuff can be set inside the fiber to give a colored article having excellent grade in vividness, light fastness and wash fastness.

The container of the present invention holds the above water-based magenta ink composition of the present invention in the container. The ink-jet printer of the present invention is equipped with the container of the present invention holding the water-based magenta ink composition on the ink-tank holder. The colored article of the present invention is dyed by the novel anthrapyridone compound represented by Formula (1) or (2) or the salt thereof, preferably by the above water-based magenta ink composition.

The water-based ink composition of the present invention can give a vivid and nearly ideal magenta color, and therefore, if used together with a yellow or cyan ink, can give a wide visible range of color tone. Further, the composition, if used together with an existing yellow, cyan or black ink which is excellent in light fastness and water fastness, can provide a recorded product with excellent grade in light fastness and water fastness.

EXAMPLE

The present invention will be described below in more details with reference to Example. "part" and "%" in the description are shown by weight unless otherwise specified.

Example 1

(1) To 450 parts of N,N-dimethylformamide were added 51.0 parts of the compound represented by Formula (3) ($R_1$=$CH_3$, $R_2$=H), 23.9 parts of sodium carbonate, 18.0 parts of cupric acetate monohydrate, and 114.0 parts of 5-acetylamino-2-sulfoaniline successively under stirring, followed by raising the temperature. The solution was reacted at 130–135° C. for 3 hrs and successively cooled, stirred at 20° C. for 30 min, filtered, washed with 300 parts of methanol, and dried to obtain 62.9 parts of the compound of Formula (4) ($R_1$=$CH_3$, $R_2$=H) as a red crystal.

To 471 parts of water was added 513 parts of 96% sulfuric acid dropwise to prepare 50% sulfuric acid, into which 61.3 parts of the compound of No.1 was added. The solution was heated under reflux (at 123° C.) for 3 hrs to react, stirred under cooling (at about 25° C.) for 1 hr, thereafter filtered and washed with 120 parts of water to obtain a red wet cake. The wet cake was added gradually under stirring into a mix solution of 2000 parts of water and 80 parts of 24% aqueous sodium hydroxide. The solution was stirred at the room temperature for 1 hr, thereafter filtered to remove a little insoluble matter. To the filtrate was added 100 parts of sodium chloride under stirring. The solution was stirred at the room temperature for 1 hr, thereafter filtered, and dried to obtain 50.2 parts of the compound of Formula (5) ($R_1$=$CH_3$, $R_2$=H) as a red crystal. λmax:523 nm (in aqueous ammonia)

(2) To 200 parts of ice water was added 0.25 parts of Lipal OH (trade name, a anionic surfactant, by Lion KK) to dissolve. 12.0 parts of cyanuric chloride was added to the solution, followed by stirring for 30 min. To the solution was added 15.5 parts of 5-amino-isophthalic acid sodium salt (purity 97.9%) at 8–10° C., followed by dropping 10% aqueous sodium hydroxide at the same temperature to maintain the pH at 5.7–6.3 for 4 hrs for the first condensation reaction to obtain the solution containing the first condensate between cyanuric chloride and 5-amino-isophthalic acid.

(3) To the reaction solution of the above (2) was added 23.5 parts of the compound of Formula (5) obtained in (1), followed by raising the temperature and dropping 10% aqueous sodium hydroxide at 60–65° C. to maintain the pH at 7.2–7.8 for 1 hr for the reaction. The solution was maintained for 1 hr at pH 8.2–8.8, and filtered to remove a little insoluble matter, to obtain the reaction solution containing the compound of No. 1.

(4) To the reaction solution obtained in above (3) was added 16.5 parts of taurine, followed by raising the temperature and dropping 10% aqueous sodium hydroxide at 98° C. to maintain the pH at 9.0 for 2 hr for the reaction. Conc.HCl was added to the reaction solution at 60–65° C. to adjust the pH to 2, followed by stirring at 60–65° C. After 1 hr, crystal was filtered to separate, washed with 250 parts of 60° C. hot water, to obtain the compound of No.2 as a red wet cake.

(5) The wet cake obtained in above (4) was added in 1500 parts of methanol, followed by heating at 60–65° C. and stirring for 1 hr. The crystal was filtered to separate, washed with methanol and dried to obtain 42.0 parts of the compound of No.2 as a red crystal. λmax:523 nm (in water, the ammonium salt); solubility in water:100 g/l or above.

Example 2

(1) To the reaction solution containing the compound of No.1 obtained as in (1)–(3) of Example 1 was added 75.0 parts of glycine, followed by increasing the temperature and dropping 10% aqueous sodium hydroxide at 95–97° C. to maintain the pH at 9.0 for 2 hr for the reaction. After filtering to remove a little insoluble matter, the filtrate solution was heated at 60–65° C., followed by adding conc.HCl under stirring to adjust the pH at 1.5 to deposit crystal. After stirring for 1 hr, the crystal was filtered to separate, and washed with water to obtain the compound of No.5 as a wet cake.

(2) The wet cake obtained in this (1) was desalted as in Example 1(5) to obtain 35.0 parts of the compound of No.5 as a red crystal. λmax:522 nm (in water, the ammonium salt); solubility in water:100 g/l or more.

Example 3

(1) To 75 parts of ice water was added 0.1 parts of Lipal OH to dissolve. 2.0 parts of cyanuric chloride was added to the solution, followed by stirring for 30 min. To the solution was added 7.1 parts of 2-naphthylamine-3,6,8-trisulfonic acid(sulfoamino G acid) (purity 65.8%) at 5–10° C., followed by dropping 10% aqueous sodium hydroxide at the same temperature to maintain the pH at 4.0–5.0 for 2 hrs for the first condensation reaction and filtering to remove a little insoluble matter to obtain the reaction solution containing the first condensate between cyanuric chloride and 2-naphthylamine-3,6,8-trisulfonic acid.

(2) To the reaction solution of the above (1) was added 4.7 parts of the compound of Formula (5) ($R_1$=$CH_3$, $R_2$=H) obtained as in Example 1 (1) and 1(2), followed by raising the temperature and dropping 10% aqueous sodium hydroxide at 60–65° C. to maintain the pH at 4–5 for 1 hr for the reaction. The solution was maintained for 1 hr at pH 6.5–7.0, and filtered to remove a little insoluble matter, to obtain the reaction solution containing the compound of No.15. The reaction solution was diluted with water to obtain 250 parts of the diluted solution, followed by heating at 60–65° C., adding 50 parts of sodium chloride and stirring for about 30 min to deposit crystal. After stirring for 1 hr, the crystal was filtered to separate, washed with 100 parts of 10% aqueous sodium chloride, and dried to obtain 8.9 parts of the sodium salt of the compound of No.15 as a red crystal. λmax:527 nm (in water); solubility in water:100 g/l or more.

Example 4

(A) Preparation of an Ink

Each water-based ink composition was produced by preparing the liquids which contain the anthrapyridone compounds (dyestuff components) of No.2, No.5 and No.15 respectively and have a composition of Table 2 as shown below, and then filtering through 0.45 μm membrane filter.

TABLE 2

| | |
|---|---|
| Dyestuff component (desalted) | 4.0 parts |
| Water | 77.0 parts |
| Glycerin | 5.0 parts |
| Urea | 5.0 parts |
| N-methyl-2-pyrrolidone | 4.0 parts |
| IPA (isopropylalcohol) | 3.0 parts |
| Butylcarbitol | 2.0 parts |
| Total | 100.0 parts |

(B) Ink-jet Printing

By using an ink-jet printer (Trade name: PICTY80L, made by NEC KK), ink-jet recordings were done on four types of recording sheets: a plain paper (Printer paper A4, TLB5A4S made by Canon KK), a special paper A (Color BJ Paper LC101 made by Canon KK), a special paper B (Coated paper for color image jetting, STX73A4 made by Sharp KK), and a glossy film (Special glossy film, MJA4SP6 made by Seiko-Epson KK).

(C) Evaluation of Recorded Image (1) Hue and Vividness

A recorded paper was subject to color determination using the colorimeter (GRETAG SPM50, made by GRETAG Co.) to calculate $L^*, a^*, b^*$ values. Hue was evaluated on the base of the $L^*, a^*, b^*$ values, and vividness was evaluated from a value calculated by the formula:

$$C^* = ((a^*)^2 + (b^*)^2)^{1/2}$$

The preferable recorded image has values in hue and vividness close to those of a color sample of standard magenta in Japan Color by Japan Printing Machinery Manufacturers Association (JNC). The values in hue and vividness of the color sample of standard magenta in the JNC's Japan Color are shown in Table 3.

TABLE 3

| JNC | Hue | | | Vividness |
|---|---|---|---|---|
| Standard | L* | a* | b* | C* |
| Magenta | 46.3 | 74.4 | −4.8 | 74.6 |

Note) Paper: the Japan Color Standard Paper (2) Light Fastness Test

A carbon arc fade meter (by Suga Testing Machine Co.) was used to irradiate carbon arc on the recorded images for 20 hours. Grade was judged according to JIS L-0841 blue scale. A color difference (ΔE) between before and after the test was measured by the above color determination system.

(3) Water Fastness Test

A recorded paper was dipped into water in a beaker, stirred for 2 min, and air-dried. The change between before and after the test was judged by the JIS color fading grey scale. Alternatively, a color difference (ΔE) between before and after the test was measured by the above color determination system.

The results of hue, vividness, light fastness test and water fastness test are listed in Table 4 on the recorded images which were printed with the water-base magenta ink compositions containing the compounds obtained in Example 1, 2 and 3 respectively.

TABLE 4

| Ex. NO. | | Hue | | | Vividness | Light fastness | Water fastness |
|---|---|---|---|---|---|---|---|
| | | L* | a* | b* | C* | Grade (ΔE) | Grade (ΔE) |
| 1 | PP | 55.8 | 59.2 | −1.6 | 59.2 | 4 (3.7) | 3–4 (8.6) |
| | SA | 54.7 | 67.4 | −2.7 | 67.5 | 3 (11.1) | 4 (2.2) |
| | SB | 51.2 | 75.5 | 1.6 | 75.5 | 3–4 (7.2) | 3–4 (5.5) |
| | GF | 50.6 | 81.2 | −6.6 | 81.5 | 4 (3.6) | 4 (3.5) |
| 2 | PP | 56.8 | 59.2 | −2.4 | 59.2 | 3–4 (8.7) | 3–4 (6.3) |
| | SA | 54.2 | 67.1 | −2.9 | 67.2 | 3 (14.1) | 4 (2.4) |
| | SB | 50.2 | 74.9 | 1.0 | 74.9 | 3 (12.4) | 4 (4.5) |
| | GF | 49.5 | 81.9 | −5.3 | 82.1 | 3–4 (10.6) | 4 (4.6) |
| 3 | PP | 58.7 | 59.1 | 4.5 | 59.3 | 3–4 (8.0) | 1 (58.6) |
| | SA | 54.7 | 68.5 | 1.9 | 68.5 | 2 (21.3) | 4 (1.3) |
| | SB | 54.5 | 75.0 | 9.8 | 75.6 | 3–4 (8.9) | 2 (19.3) |
| | GF | 55.3 | 79.6 | 4.4 | 79.7 | 4 (2.8) | 4 (3.8) |

(note)
The abbreviations in Table 4 are as follows:
PP: Plain Paper; SA: Special Paper A; SB: Special Paper B; DF: Glossy Film The anthrapyridone dyestuff of the present invention is suitable for an ink-jet magenta dyestuff because it has values in hue and brightness close to those of the JNC standard magenta. The dyestuff of the present invention also, when used on a special paper, can provide good light fastness and water fastness. The comparison of Example 1 and 2 with Example 3 reveals that the dyestuff of the present invention, if it has X and/or Y having carboxy in Formula as illustrated above, can provide a greatly improved water fastness when used on a plain paper. Further, the dyestuffs of No.2, No.5 and No.15 obtained in Example 1 to 3 have their water-solubilities of 100 g/l or more under an alkaline condition (pH 8–9) and therefore enable to prepare stable inks for ink-jetting. Furthermore, they are widely and easily usable because they can provide a high concentration of ink.

Example 5

To the reaction solution containing the compound of No.1 obtained as in (1)–(3) of Example 1 was added 8.9 parts of β-alanine, followed by raising the temperature and dropping 10% aqueous sodium hydroxide at 90–95° C. to maintain the pH at 9.0 for 1.5 hr for the reaction and further to maintain the pH at 10.0 for 1 hr to complete the reaction. After filtering to remove a little insoluble matter, the filtrate solution was heated at 60–65° C., followed by adding 20% by mass of sodium chloride relative to the total liquid under stirring and then adding conc.HCl to adjust the pH at 1.5 to deposit crystal. After stirring for 1 hr, the crystal was filtered to separate, washed with 250 parts of water and then with 250 parts of methanol, and dried to obtain 37.0 parts of the compound of No.7 as a red crystal. λmax:521 nm (in water, the ammonium salt).

Example 6

(1) To the reaction solution containing the compound of No.1 obtained as in (1)–(3) of Example 1 was added 15% by mass of sodium chloride relative to the reaction solution to salt out, followed by stirring for 30 min at the room temperature and filtering to obtain the compound of No.1 as a cake.

(2) The cake obtained in above (1) was stirred with 500 parts of water. To the solution was added 20.0 parts of L-aspartic acid, followed by maintaining the pH at 9.5 at 90–95° C. for 6 hrs for the reaction. After filtering to remove a little insoluble matter, the filtrate solution was heated at 60–65° C., followed by adding conc.HCl under stirring to adjust the pH at 1.5. After stirring for 1 hr, the deposited crystal was filtered to separate to obtain a red wet cake.

(3) 175 parts of the wet cake obtained by the above (2) was heated with 800 parts of methanol under reflux for 1 hr, followed by filtering, washing with methanol, and drying to obtain 21.2 parts of the compound of No.8 as a crystal. λmax:523 nm (in water, the ammonium salt).

Example 7

(1) The wet cake of the compound of No.1 obtained as in Example 6 (1) was stirred with 600 parts of water to heat, followed by maintaining the temperature at 85–90° C. To the solution was added 20.0 parts of iminodiacetic acid, followed by dropping 10% aqueous sodium hydroxide to maintain the pH at 10.0 for 2.5 hrs to complete the reaction. After filtering to remove a little insoluble matter, the filtrate solution was heated at 65–70° C., followed by adding 15% by mass of sodium chloride relative to the total liquid and then adding conc.HCl to adjust the pH at 2. After stirring for 1 hr, the deposited crystal was filtered to obtain a wet cake containing the compound of No.90.

(2) The wet cake obtained in above (1) was stirred with 500 parts of methanol and 300 parts of water to heat at 65° C. After 1 hr, the crystal was filtered to separate, washed with methanol, and dried to obtain 42.5 parts of the compound of No.90 as a red crystal. λmax:522 nm (in water, the ammonium salt).

Example 8

(1) The wet cake of the compound of No.1 obtained as in Example 6 (1) was stirred with 800 parts of water to heat at 80–85° C. To the solution was added 10.2 parts of 2-diethylamino-ethylamine, followed by dropping 10% aqueous sodium hydroxide to maintain the pH at 10 for 2 hrs for the reaction. The reaction solution was filtered to remove a little insoluble matter, followed by adding conc.HCl to the filtrate to adjust the pH at 1.5 to deposit crystal. After stirring at 70° C. for 30 min, the crystal was filtered to obtain a wet cake containing the compound of No.89.

(2) The wet cake obtained in this (1) was stirred with 800 parts of water to heat at 65–70° C. for 1 hr. The crystal was filtered to separate, washed with hot water, and dried to obtain 26.1 parts of the compound of No.89 as a red crystal. λmax:525 nm (in water, the ammonium salt).

Example 9

To the reaction solution containing the compound of No.1 obtained as in (1)–(3) of Example 1 was added 11.4 parts of 3-diethylamino-propylamine, followed by stirring to heat at 80–85° C. and dropping 10% aqueous sodium hydroxide to maintain the pH at 10 for 2 hr for the reaction. The reaction solution was filtered to remove a little insoluble matter, followed by heating the filtrate at 50–60° C., and then adding conc.HCl under stirring to adjust the pH at 2 to deposit crystal. After stirring for 30 min, the crystal was filtered to separate, washed with hot water, and dried to obtain 42.0 parts of the compound of No.88 as a red crystal. λmax:524 nm (in water, the ammonium salt).

INDUSTRIAL APPLICABILITY

The novel anthrapyridone compound of the present invention is excellent in water-solubility, stable in storing the solution and characterized by having a good ability to filter through a membrane filter in the production process of an ink composition. The compound is highly safe for a living body. Furthermore, the ink composition of the present invention using the novel anthrapyridone compound does not show a crystal deposition after a long storage, a change in property and a color change, so that it has good storage stability. The ink composition of the present invention, when used as a magenta ink for ink-jet recording, can provide a printed matter with excellent grade in light fastness and water fastness. Furthermore, the composition also, when used together with a yellow, cyan or black dye, can give an ink-jet recorded matter that is excellent in light fastness and water fastness. The composition also can provide a vivid printed surface as well as an ideal magenta color. The composition, when used together with a yellow or cyan ink, can provide a wide visible ray range of color tone.

Therefore, the ink composition of the present invention is very useful as a magenta ink for ink-jet recording.

What is claimed is:

1. A novel anthrapyridone compound represented by Formula (1) as described below or the salt thereof

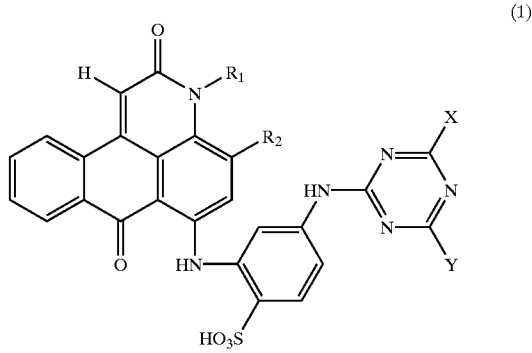

wherein, $R_1$ is hydrogen, an alkyl group, a hydroxy lower alkyl group, cyclohexyl, a mono- or di-alkylaminoalkyl group, or a cyano lower alkyl group; $R_2$ is hydrogen, methyl, ethyl, phenoxy which may be substituted, sulfo or carboxy; X and Y represent independently chloro, hydroxy, an alkoxy group, phenoxy which may be substituted with the substituents selected from the group consisting of sulfo, carboxy, acetylamino, amino, and hydroxy, a mono- or di-alkylamino group having sulfo or carboxy, anilino which may be substituted with one or two substituents selected from the group consisting of sulfo and carboxy, naphthylamino, the naphthyl may be substituted with sulfo, or a mono- or di-alkylaminoalkylamino group, except that X and Y are respectively any groups selected from the group consisting of chloro, hydroxy and anilino which may be substituted with one or two substituents selected from the group consisting of sulfo and carboxy, if $R_2$ is hydrogen.

2. A novel anthrapyridone compound or the salt thereof according to claim 1, wherein said compound is represented by Formula (2) as described below:

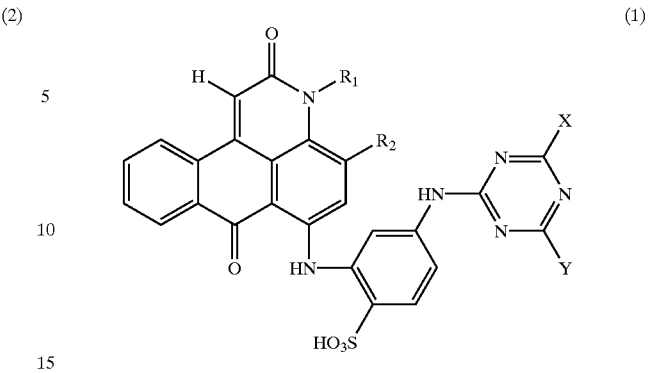

or Formula (2) or the salt thereof:

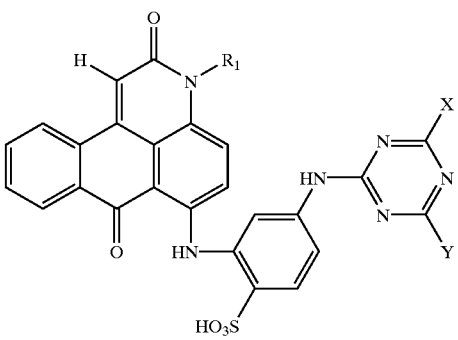

wherein $R_1$ is hydrogen or methyl; $R_2$ is hydrogen, methyl, ethyl, phenoxy which may be substituted, sulfo or carboxy; X is anilino having two carboxy groups; and Y is hydroxy, anilino having two sulfo groups, an alkylamino group having sulfo or carboxy, or a dialkylaminoalkylamino group.

9. A novel anthrapyridone compound or the salt thereof according to claim 8, wherein said anilino having two carboxy groups is 3,5-dicarboxyanilino, said alkylamino group having sulfo or carboxy is 2-sulfoethylamino, carboxymethylamino, 2-carboxyethylamino or 1-carboxyethylamino, diethylaminoethylamino, or diethylaminopropylamino.

10. A water-based magenta ink composition that contains the anthrapyridone compound or the salt thereof according to claim 1 as a dyestuff component.

11. A water-based magenta ink composition according to claim 10, wherein said composition contains an organic solvent.

12. A water-based magenta ink composition according to claim 10 or 11, wherein the content of inorganic salt included in the dyestuff component is 1% by mass or less.

13. A water-based magenta ink composition according to claim 12, wherein said composition is prepared for ink-jet recording.

14. A method for ink-jet recording comprising ejecting ink droplets in response to record signals to record into a recording material, said ink droplets comprising the water-based magenta ink composition according to claim 13.

15. A method for ink-jet recording according to claim 14, wherein said recording material is an information transmission sheet.

16. A container holding the water-based magenta ink composition according to claim 13.

17. An ink-jet printer equipped with the container according to claim 16.

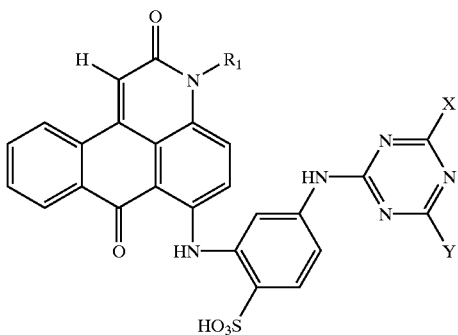

wherein, $R_1$ is hydrogen or an alkyl group; X and Y represent independently chloro, hydroxy, an alkoxy group, phenoxy which may be substituted with the substituents selected from the group consisting of sulfo, carboxy, acetylamino, amino, and hydroxy, an alkylamino group having sulfo or carboxy, anilino which may be substituted with one or two substituents selected from the group consisting of sulfo and carboxy, naphthylamino, the naphthyl may be substituted with sulfo, or a dialkylaminoalkylamino group, except that X and Y are respectively any groups selected from the group consisting of chloro, hydroxy and anilino which may be substituted with one or two substituents selected from the group consisting of sulfo and carboxy.

3. A novel anthrapyridone compound or the salt thereof according to claim 1 or 2, wherein X is anilino which may be substituted with one or two substituents selected from the group consisting of sulfo and carboxy, or naphthylamino, the naphthyl may be substituted with sulfo; and Y is chloro, hydroxy, an alkoxy group, phenoxy which may be substituted with the substituents selected from the group consisting of sulfo, carboxy, acetylamino, amino, and hydroxy, anilino, which may be substituted with one or two substituents selected from the group consisting of sulfo and carboxy, an alkylamino group having sulfo or carboxy, or a dialkylaminoalkylamino group.

4. A novel anthrapyridone compound or the salt thereof according to claim 1 or 2, wherein $R_1$ is hydrogen or methyl; X is anilino substituted with one or two substituents selected from sulfo and carboxy; and Y is hydroxy, methoxy, phenoxy which may be substituted with the substituents selected from the group consisting of sulfo, carboxy, acetylamino, amino, and hydroxy, anilino having sulfo, an alkylamino group having sulfo or carboxy, or a dialkylaminoalkylamino group.

5. A novel anthrapyridone compound or the salt thereof according to claim 1 or 2, wherein X is naphthylamino substituted with sulfo; and Y is chloro, hydroxy, methoxy, phenoxy which may be substituted with the substituents selected from the group consisting of sulfo, carboxy, acetylamino, amino, and hydroxy, or an alkylamino group having sulfo or carboxy.

6. A novel anthrapyridone compound or the salt thereof according to claim 1 or 2, wherein $R_1$ is hydrogen or methyl; X is naphthylamino substituted with three sulfo groups; and Y is chloro, hydroxy, or phenoxy.

7. A novel anthrapyridone compound or the salt thereof according to claim 6, wherein said naphthylamino substituted with three sulfo groups is the 2-naphthylamino or 1-naphthylamino that has said three sulfo groups at the 3-, 6-, and 8-positions or at the 4-, 6-, and 8-positions.

8. A novel anthrapyridone compound represented by Formula (1) or the salt thereof:

18. A colored article including the anthrapyridone compound or the salt thereof according to any one of claims 1 to 9.

19. An anthrapyridone compound represented by Formula (5) as shown below:

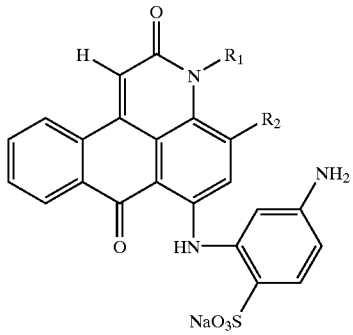

(5)

wherein, $R_1$ is hydrogen, an alkyl group, a hydroxy lower alkyl group, cyclohexyl, a mono- or di-alkylaminoalkyl group, or a cyano lower alkyl group; and $R_2$ is hydrogen, methyl, ethyl, phenoxy which may be substituted, sulfo or carboxy; except that if $R_1$ is hydrogen or methyl, $R_2$ is hydrogen.

20. An anthrapyridone compound represented by Formula (6) as shown below:

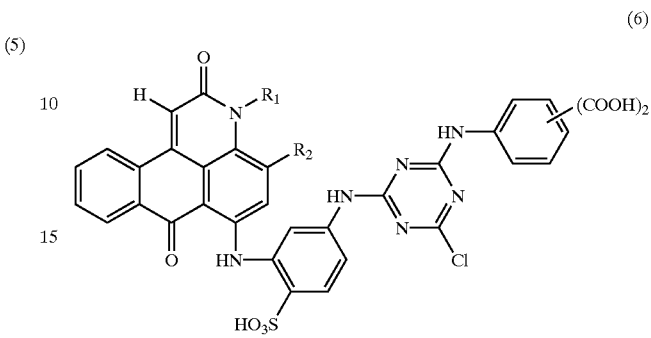

(6)

wherein, $R_1$ is hydrogen, an alkyl group, hydroxyethyl, cyclohexyl, a dialkylaminoalkyl group or cyanoethyl; $R_2$ is hydrogen, methyl, ethyl, phenoxy which may be substituted, sulfo or carboxy.

* * * * *